(12) United States Patent
Solanki et al.

(10) Patent No.: US 8,038,629 B2
(45) Date of Patent: Oct. 18, 2011

(54) DIGITAL ENDOTRACHEAL TUBE SOUND ACQUISITION AND LOCALIZATION DEVICE

(75) Inventors: Daneshvari R. Solanki, League City, TX (US); Thomas K. Doan, Plano, TX (US); William E. McGrady, II, Texas City, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 342 days.

(21) Appl. No.: 12/244,577

(22) Filed: Oct. 2, 2008

(65) Prior Publication Data
US 2009/0099479 A1   Apr. 16, 2009

Related U.S. Application Data

(60) Provisional application No. 60/977,034, filed on Oct. 2, 2007.

(51) Int. Cl.
| | |
|---|---|
| *A61M 15/00* | (2006.01) |
| *A61M 16/00* | (2006.01) |
| *A61B 5/05* | (2006.01) |
| *A61B 5/08* | (2006.01) |
| *A61B 5/103* | (2006.01) |
| *A61B 5/117* | (2006.01) |
| *A61B 17/00* | (2006.01) |

(52) U.S. Cl. ............. 600/587; 128/200.24; 128/202.22; 128/207.14; 128/207.16; 600/424; 600/529; 600/538; 600/593; 606/202; 606/203

(58) Field of Classification Search ............. 128/200.24, 128/202.22, 207.14, 207.16; 600/424, 529, 600/538, 586, 593; 606/202, 203

See application file for complete search history.

(56) References Cited

U.S. PATENT DOCUMENTS

| | | | | |
|---|---|---|---|---|
| 3,848,605 A | * | 11/1974 | Harautuneian et al. | 128/207.15 |
| 4,173,228 A | * | 11/1979 | Van Steenwyk et al. | 600/409 |
| 4,346,702 A | * | 8/1982 | Kubota | 128/207.14 |
| 4,630,606 A | * | 12/1986 | Weerda et al. | 128/207.14 |
| 5,005,573 A | * | 4/1991 | Buchanan | 128/207.14 |
| 5,099,845 A | * | 3/1992 | Besz et al. | 600/424 |
| 5,181,517 A | * | 1/1993 | Hickey | 600/486 |
| 5,257,636 A | * | 11/1993 | White | 128/897 |
| 5,295,489 A | * | 3/1994 | Bell et al. | 600/528 |
| 5,331,967 A | * | 7/1994 | Akerson | 600/529 |
| 5,360,003 A | * | 11/1994 | Capistrano | 128/207.15 |
| 5,421,325 A | * | 6/1995 | Cinberg et al. | 128/200.26 |
| 5,445,144 A | * | 8/1995 | Wodicka et al. | 128/207.14 |

(Continued)

FOREIGN PATENT DOCUMENTS

WO   WO 03015610 A2 *   2/2003

*Primary Examiner* — Max Hindenburg
*Assistant Examiner* — Sean Dougherty
(74) *Attorney, Agent, or Firm* — Robert W Strozier

(57) ABSTRACT

An apparatus and method for determining proper endotreachal placement is disclosed. The apparatus includes an audio receiver having a body, a microphone mount in a center thereof the body and an audio cavity, an audio processing unit; and a signal cable connected at a first end to the microphone and at a second end, where the receiver is adapted to be positioned in a suprasternal notch of a patient and the acoustic signal detected after inflation of a balloon associated with an endotracheal tube. The method uses the apparatus to detect and analyze an audio signal. The audio signal is then used to confirm endotracheal tube placement.

9 Claims, 6 Drawing Sheets

U.S. PATENT DOCUMENTS

| | | | |
|---|---|---|---|
| 5,487,731 A * | 1/1996 | Denton | 604/100.01 |
| 5,560,351 A * | 10/1996 | Gravenstein et al. | 128/200.26 |
| 5,570,671 A * | 11/1996 | Hickey | 600/486 |
| 5,591,130 A * | 1/1997 | Denton | 604/100.02 |
| 5,697,375 A * | 12/1997 | Hickey | 600/486 |
| 5,785,051 A * | 7/1998 | Lipscher et al. | 128/207.15 |
| 6,161,537 A * | 12/2000 | Gravenstein et al. | 128/200.26 |
| 6,164,277 A * | 12/2000 | Merideth | 128/207.14 |
| 6,349,720 B1 * | 2/2002 | Clark | 128/200.26 |
| 6,705,319 B1 * | 3/2004 | Wodicka et al. | 128/207.14 |
| 6,860,264 B2 * | 3/2005 | Christopher | 128/200.26 |
| RE41,066 E * | 12/2009 | Martinelli et al. | 600/424 |
| 7,878,980 B2 * | 2/2011 | Ricciardelli | 600/533 |
| 2003/0018276 A1 * | 1/2003 | Mansy et al. | 600/529 |
| 2003/0034035 A1 * | 2/2003 | Raphael | 128/207.14 |
| 2006/0081255 A1 * | 4/2006 | Miller et al. | 128/207.14 |
| 2007/0129667 A1 * | 6/2007 | Tiedtke et al. | 604/27 |
| 2007/0167781 A1 * | 7/2007 | Vortman et al. | 600/443 |
| 2007/0244423 A1 * | 10/2007 | Zumeris et al. | 604/22 |
| 2008/0030104 A1 * | 2/2008 | Prus | 310/334 |
| 2009/0018446 A1 * | 1/2009 | Medan et al. | 600/439 |
| 2010/0256476 A1 * | 10/2010 | Wood | 600/409 |
| 2010/0256482 A1 * | 10/2010 | Peters et al. | 600/424 |
| 2010/0319702 A1 * | 12/2010 | Wood et al. | 128/207.14 |

* cited by examiner

DIGITAL ENDOTRACHEAL TUBE SOUND ACQUISITION AND LOCALIZATION DEVICE

RELATED APPLICATIONS

This application claim priority to and the benefit of U.S. Provisional Application Ser. No. 60/977,034, filed Oct. 2, 2007.

BACKGROUND OF THE INVENTION

1. Field of the Invention

The present invention relates to an apparatus and method for confirming proper endotracheal tube placement.

More particularly, the present invention relates to an apparatus and method for confirming proper endotracheal tube placement, where the apparatus includes a microphone and an audio signal receiver and output unit capable of receiving sound produced by squeezing a pilot balloon of the endotracheal tube filled with a mixture of a gas (such as air) and a liquid (such as water) and the method includes placing the microphone on a suprasternal notch of a patient, inserting the endotracheal tube, filling the pilot balloon with a mixture of a gas and a liquid, squeezing the balloon and analyzing the sound generated by the balloon in a digital sound acquisition and localization unit to confirm proper endotracheal tube placement.

2. Description of the Related Art

The most important job an anesthesiologist does is to place an endotracheal tube (ET) in the trachea when general anesthesia with a secure airway is indicated. The inability to place the ET in the trachea or to misplace the ET in the esophagus can lead to disastrous results and even death. The ET has a pilot balloon that communicates with the cuff on the endotracheal tube. When the pilot balloon is inflated with air/gas, it inflates the endotracheal tube cuff. This produces a seal so the chances of gastric contents entering the trachea are minimized. The endotracheal tube cuff can be felt in the suprasternal notch when the pilot balloon is compressed. Presently there are three ways to confirm proper placement of the endotracheal tube: (1) water vapor mist in the endotracheal tube; (2) auscultation of bilateral breath sounds when oxygen or air is deliver through a reservoir bag or Ambu bag; and (3) detection of carbon dioxide either on a capnograph or a disposable $CO_2$ monitor, which is today considered the gold standard by the American Association of Anesthesiologists. But none of these methods are 100% confirmatory.

United States Published Patent Application No. 20030018276 discloses a system and method for use in detecting an endotracheal tube location within a body electronically detects indigenous breath sounds emanating from a region of the body and processes the detected indigenous breath sounds to generate a parameter representative of an acoustic characteristic of the body associated with the endotracheal tube location within the body. The system and method generates an output indicative of the endotracheal tube location within the body based on the parameter representative of the acoustic characteristic of the body. The system uses a speaker to generate an input signal that is then detected by an microphone or other audio detector.

U.S. Pat. No. 6,349,720 disclosed an endotracheal tube having an audio aid for indicating the accurate placement thereof. In a first preferred embodiment, the invention comprises a cuffed ETT having distal and proximal ends, the latter having a mechanical noise-making apparatus formed thereon that provides an audible signal when air passes therethrough. In a second preferred embodiment, the invention comprises the combination of a cuffed ETT having distal and proximal ends and an insertion rod for stiffening the ETT during insertion. The insertion rod is coupled to an electrically-powered noise maker formed upon the distal end thereof to produce an audible sound before air flow through the ETT is established. In both embodiments the correct placement is determined by the unaided ear hearing the noise coming from both sides of the chest. If sound is from one side only the insertion is too deep. If the sound is heard from the stomach the ETT is in the esophagus instead of trachea and should be pulled out and reinserted.

U.S. Pat. No. 5,445,144 disclosed an apparatus and method for acoustically guiding a distal end of a tube within a body. The apparatus and method generates an incident sound pulse in the tube which propagates into the body, detects sound pulses resulting from the incident sound pulse and from reflected sound pulses from within the body, and processes the detected sound pulses to guide insertion of the distal end of the tube within the body. The apparatus and method provides an indication of the position of the distal end of the tube within the body conduit, estimates dimensions of the body conduit adjacent the distal end of the tube, and determines if the tube is obstructed.

Although these methods and their associated apparatus are known, there is still an need in the art for apparatuses and methods that improve the ability to confirm proper ET placement.

SUMMARY OF THE INVENTION

The present invention provides an apparatus for confirming proper endotracheal tube placement including an audio receiver such as a microphone (e.g., solid state condensed microphone, an electrocouplet microphone, etc.). The microphone is connected to a digital audio signal processor. The microphone is adapted to be placed on a patient at a site where crepitus sounds can be efficiently detected and analyzed such as placement in a suprasternal notch of a patient. After the placement of the tube, the pilot balloon filled with a mixture of a gas (such as air) and a liquid. Proper placement can be confirmed by the audio signature produced by squeezing the pilot balloon that produces crepitus and detected by the microphone placed in the suprasternal notch or other site of the body that is capable of yielding a clear audio signal. The digital audio signal processor includes at least one output component designed to generate a human cognizable output, where the output component can be a speaker, a speaker with voice generation capability, a display, indicator lights, a tactile switch (a device adapted to generate a touch discernible output), vibrator, and/or any other type of output device that generates a human cognizable output. The processor can also include a memory, a mass storage device, a port for an external mass storage device, communication hardware and software (wired and/or wireless) for connecting the processor to an external computer or distributed computer network such as an intranet or internet, a port for connection to a fixed or portable computer (desktop, server, personal digital assistance, or any other digital based computing device), and/or a port for connection to a hard copy output device.

The present invention also provides method including the step of placing a receiver of this invention at a site on a patient where crepitus sounds can be efficiently detected and analyzed such as placing the receive in a suprasternal notch of a patient. Once the receiver is in place, an endotracheal tube having a pilot balloon is inserted into the patient. The balloon is filled with a mixture of a gas (such as air) and a liquid and is adapted to generate a well characterized sound when squeezed. After initial tube placement and inflating the pilot balloon with the gas/liquid mixture, squeezing the balloon produces the sound which is detected by the receiver as an audio signal. The received audio signal is then forwarded to an audio signal processor in electrical communication with the receiver. The processed signal is then analyzed to determine if the signal conforms to a signal corresponding to a proper placement of the tube in the patient. The processor can output the signal via an output component concurrent or after determination. If the signal does not indicate proper placement either based on the output signal directly or from the processor determination, then the tube can be repositioned until the proper signal is detected, analyzed and determined.

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

Figures 1A, 1B:
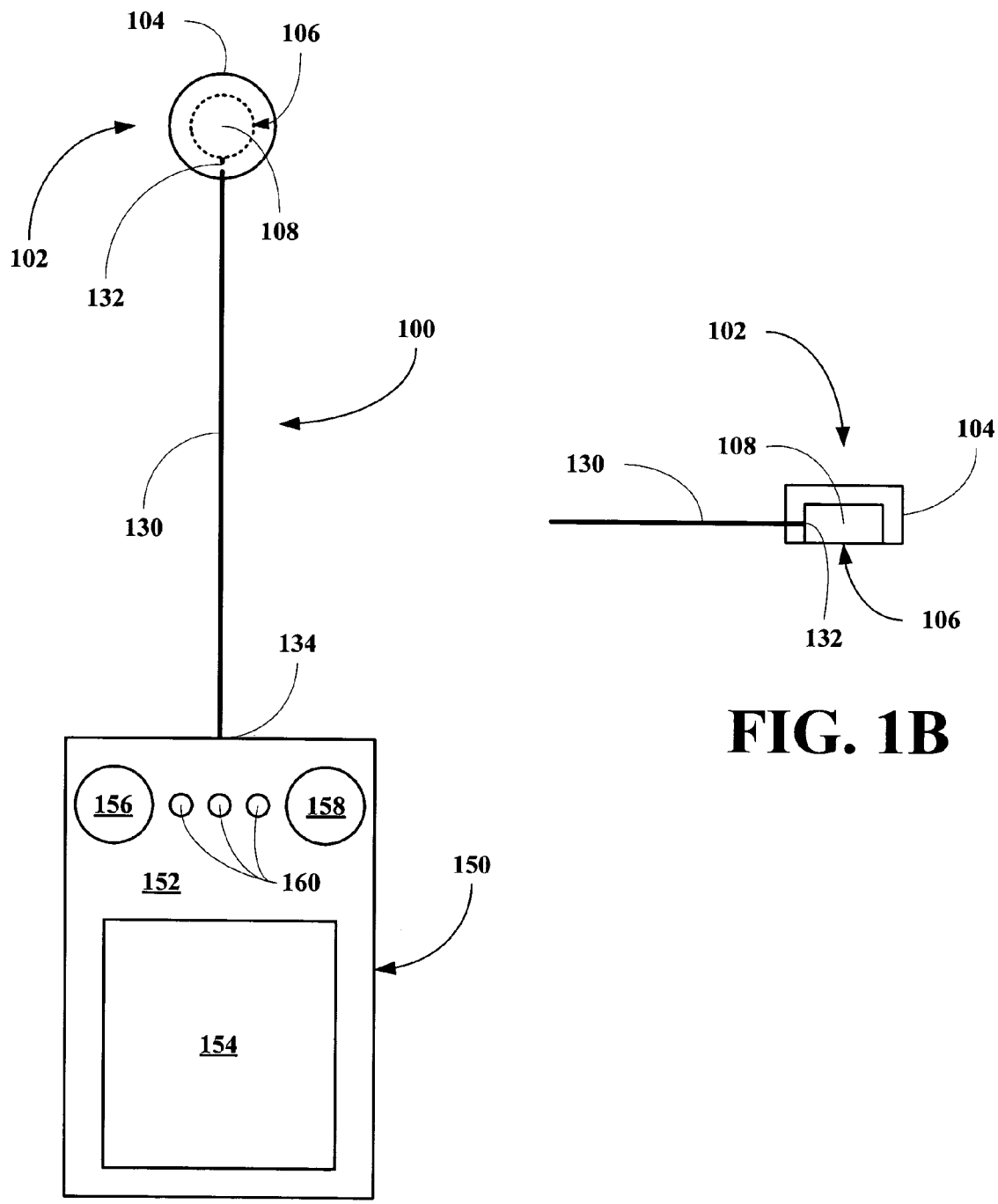
FIGS. 1A&B depict an embodiment of an apparatus to confirm proper placement of an endotracheal tube in a patient.

The inventors have found that an apparatus and an associated method can be constructed and implemented for confirming proper placement of an endotracheal tube in a patient whenever an endotracheal tube is required such as when a patient if undergoing a medical procedure requiring general anesthesia, has an obstructed breathing pathways, or is in need of ventilation. Proper endotracheal tube placement is critical to patient health and safety for improper placement can lead to serious complications including death. The inventors have found that by filling a pilot balloon of an endotracheal tube with a mixture of a gas and a liquid, the sound produced by the balloon as it is squeezed can be used to determine proper endotracheal tube placement. The inventors have found that the sound from the balloon can be used to distinguish between a properly placed endotracheal tube and improperly placed tube. The inventors have also found that the sound from the balloon can be used to determine the type of improper placement including placement in the esophagus or placement that ventilates only one lung. The inventors have found that the sound can be detected efficiently via a microphone disposed on the patient at a site sufficient to clearly detect the sound, a crepitus produced by air bubbles moving through the liquid of the gas/liquid mixture used to fill the balloon. The inventors have found that if the tube is placed in the esophagus, the crepitus is not heard well as there is a column of air in the trachea interposed between the microphone and the ballon—air is a bad conductor of sound. The sound detected if the tube ventilates only one lung is also distinct from the sound produced by a properly positioned endotracheal tube.

The present invention broadly relates to an apparatus for confirming proper endotracheal tube placement including an endotracheal tube having a pilot balloon filled with a gas air mixture. The apparatus also includes an audio or acoustic detection system and optionally an audio analyzer system. The audio detection system includes an audio microphone or other audio sensing device capable of detecting audio frequencies in a range corresponding to a sound generated by the pilot balloon when it is squeezed and release one or more times. The audio detector system also includes an audio sound card capable of receiving and amplifying the sound in a digital format. The sound in digital format can then be played, displayed or reproduced for touch. The sound in digital format can also be analyzed to determine if it is consistent with proper endotracheal tube placement or improper placement. The apparatus can also include output devices to inform an user if endotracheal tube placement in proper or improper in a variety of different display formats. The apparatus can be comprise two or more substantially separate components or can be a single component. The present invention also broadly relates to method for making and using same. Different embodiments of the apparatus are described more fully in the detailed description of the drawings section.

Clinically, the sound of air bubbles in a balloon filled with a gas/liquid mixture is a useful tool for well trained practitioners to determine proper endotracheal tube. However, the technique depends on the practitioner. The inventors have designed a specialized medical apparatus adapted to allow all medical personnel including highly trained doctors and nurses to emergency medical personnel, military medical personnel, and first responders to quickly and reliably determine proper endotracheal tube placement in a non-invasive method.

The that includes an audio bell including a microphone capable of detecting an audio signal generated by the tracheal crepitus, which occurs within a given frequency range. The apparatus also includes an audio processor adapted to receive the audio signal detected from the microphone and analyze the signal. The signal analysis gives rise to a straight forward way to confirm proper endotracheal tube placement. Besides the anesthesiologists, nurse anesthesiologists, anesthesiologists in training, or other medical personnel will be able to use the apparatus to confirm proper endotracheal tube placement. Such a medical instrument will have application: 1) during medical emergencies in the field administered by paramedics or other medical professionals and 2) during medical emergencies in military theaters where night medical operation or operation with limited light are performed. The medical apparatuses of this invention and the associated methods are ideal for endotracheal tube localization to determine and confirm proper endotracheal tube placement before the first breath is given. Such apparatuses and methods are capable of reducing or preventing gastric insufflation and regurgitation of gastric content.

The apparatus of this invention is not an electronic stethoscope. It does not electronically filter nor enhance the audio signal beyond the normal range of human hearing. The apparatus is unique in its use of a high-fidelity microphone and signal processor having a 24-bit-48 khz sampling rate, which was not achievable with off-the-shelf components until recent year. The heart of the system is the sum of an excellent response and fidelity of an electrocouplet microphone picking up sound from a high quality audio receiver such as the head of a high quality stethoscope. Suitable stethoscopes includes stethoscopes made by Littman. Suitable high-fidelity and large sampling rate audio processor include an Audigy 2 Z95 soundblaster card made by Creative Inc. Never has such a combination of high-fidelity, high bit-rate sampling and acquisition strictly designed around a solid, high-quality diaphragm stethoscope with excess vibration being absorbed with the insulation foam to reduce vibration and, therefore, boost the signal-to-noise ratio to take advantage of the 108 dB audio processor card. The audio components are all adapted to determine the sound characteristics of endotracheal tube tubes in tracheal positions and esophageal positions. The signal picked up from the crepitus is filtered through a specialized frequency window specifically designed to confirm the placement of the endotracheal tube. This device will have further development potential once the sound characteristics for endotracheal tube placement have been documented and approved by peer-based review such as the ASA or APSF (Anesthesia Patient Safety Foundation).

An embodiment of this invention includes a Littman Cardiology II stethoscope having the ear part cut off leaving a 120 mm length of tubing. The dual lumen chamber of the stethoscope bell receiver was sliced into a single orifice having a diameter of 12 mm. Into the orifice, the inventors mounted an electrocouplet microphone having a frequency response of 70-16,000 Hz with an inline battery amplification and impedence of 1000 Ohms±20% at 1000 Hz and sensitivity of −65 dB±3 dB at 1000 Hz. The microphone includes a 1.37 mm cord having a 2 mm diameter and ending with a 3.5 mm standard audio jack. The first 112 mm of remaining ear part tube was filed or encased in low-density foam to dampen excess vibration resulting from rubbing and external noise influence on the tube before the electrocouplet microphone pick-up. Artifact can be introduced by rubbing of tube especially as the patient inhales or exhales, cardiac or thoracic fasciculations, hyperthermic shake, external noise from talking, breathing, and etc. The foam isolates the sound within the tube in the noisy operating room environment. The microphone is then plugged into a Soundblaster Audigy 2 Z95 notebook audio card with 24 bit-48 kHz sampling available from Creative Inc. and recorded using standard lossless ".wav" file extension without the use of an audio compression or a filter to maintain fidelity and clarity of sound.

DETAILED DESCRIPTION OF DRAWINGS

General Embodiments

Referring now to FIGS. 1A&B, an embodiment of an apparatus of this invention, generally 100, is shown to include an audio receiving unit 102 having a body 104. In a center 106 of the body 104 is mounted an audio receiver 108 such as a microphone. In this embodiment 100, the receiver 108 is designed to come into contact with the skin of the patient. A fluid such as the fluid used in ultrasound can be used to improve audio contact between the receiver and the skin.

The apparatus 100 also includes a signal cable 130 connected at a first end 132 to the receiver 108 and at a second end 134 to an audio processing unit 150.

The processing unit 150 include a housing 152. The processing unit 152 can include one or more of a visual display component 154, a speaker 156, a tactile component 158 or indicator lights 160. The visual display component 154 is adapted to produce a visual image corresponding to the received audio signal and an analysis of whether the received audio signal evidences a proper tube placement. The visual display can be a display of the received signal relative to a signal from a properly placed tube or a display of the received signal and a message indicated proper or improper placement. The speaker 156 is adapted to produce an audio signal either corresponding to the received audio signal or to produce an indication that the signal corresponds either to a proper or improper placement of the tube such as a voice saying good or bad placement. The tactile component 158 is adapted to produce touch cognizable pulses to indicate proper or improper tube placement. The indicator lights 160 are adapted to produce lights indicating proper or improper tube placement. The processing unit 150 can include all of any combination of these output components. Moreover, each output component can be designed not only to evidence proper tube placement, but to also evidence the nature of the improper tube placement such as placement in the esophagus, a placement ventilating a single lung, a placement with an improper seal, etc.

Figures 2A, 2B:
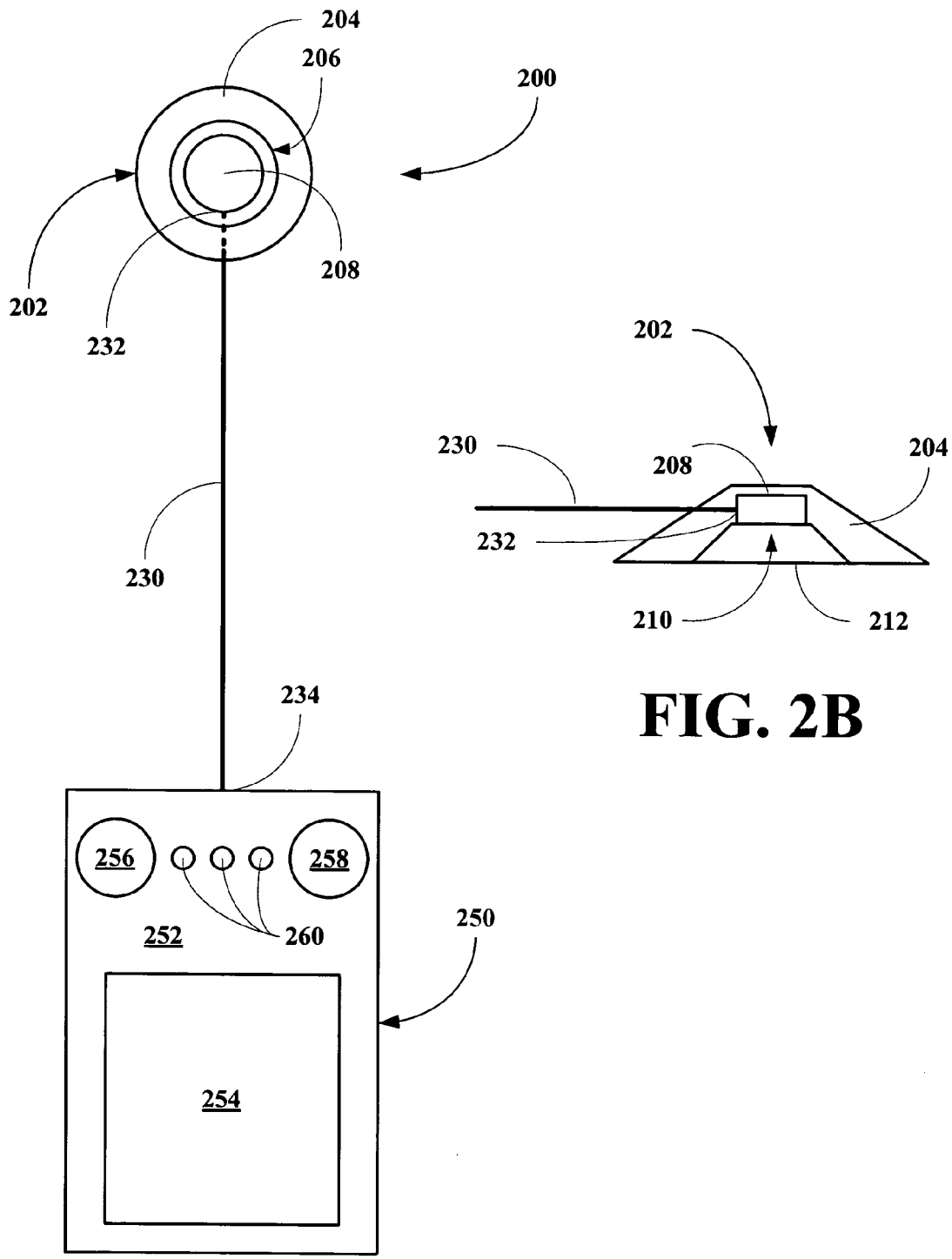
FIGS. 2A&B depict another embodiment of an apparatus to confirm proper placement of an endotracheal tube in a patient.

Referring now to FIGS. 2A&B, an embodiment of an apparatus of this invention, generally 200, is shown to include an audio receiving unit 202 having a body 204. In a center 206 of the body is mounted a receiver 208. The receiving unit 202 also includes an audio cavity 210. The receiving unit 202 may also include a diaphragm 212 so that the cavity 210 is defined between the diaphragm 212 and the receiver 208.

The apparatus 200 also includes a signal cable 230 connected at a first end 232 to the microphone 108 and at a second end 234 to an audio processing unit 250.

The processing unit 250 include a housing 252. The processing unit 252 can include one or more of a visual display component 254, a speaker 256, a tactile component 258 or indicator lights 260. The visual display component 254 is adapted to produce a visual image corresponding to the received audio signal and an analysis of whether the received audio signal evidences a proper tube placement. The visual display can be a display of the received signal relative to a signal from a properly placed tube or a display of the received signal and a message indicated proper or improper placement. The speaker 256 is adapted to produce an audio signal either corresponding to the received audio signal or to produce an indication that the signal corresponds either to a proper or improper placement of the tube such as a voice saying good or bad placement. The tactile component 258 is adapted to produce touch cognizable pulses to indicate proper or improper tube placement. The indicator lights 260 are adapted to produce lights indicating proper or improper tube placement. The processing unit 250 can include all of any combination of these output components. Moreover, each output component can be designed not only to evidence proper tube placement, but to also evidence the nature of the improper tube placement such as placement in the esophagus, a placement ventilating a single lung, a placement with an improper seal, etc.

Figures 3A, 3B:
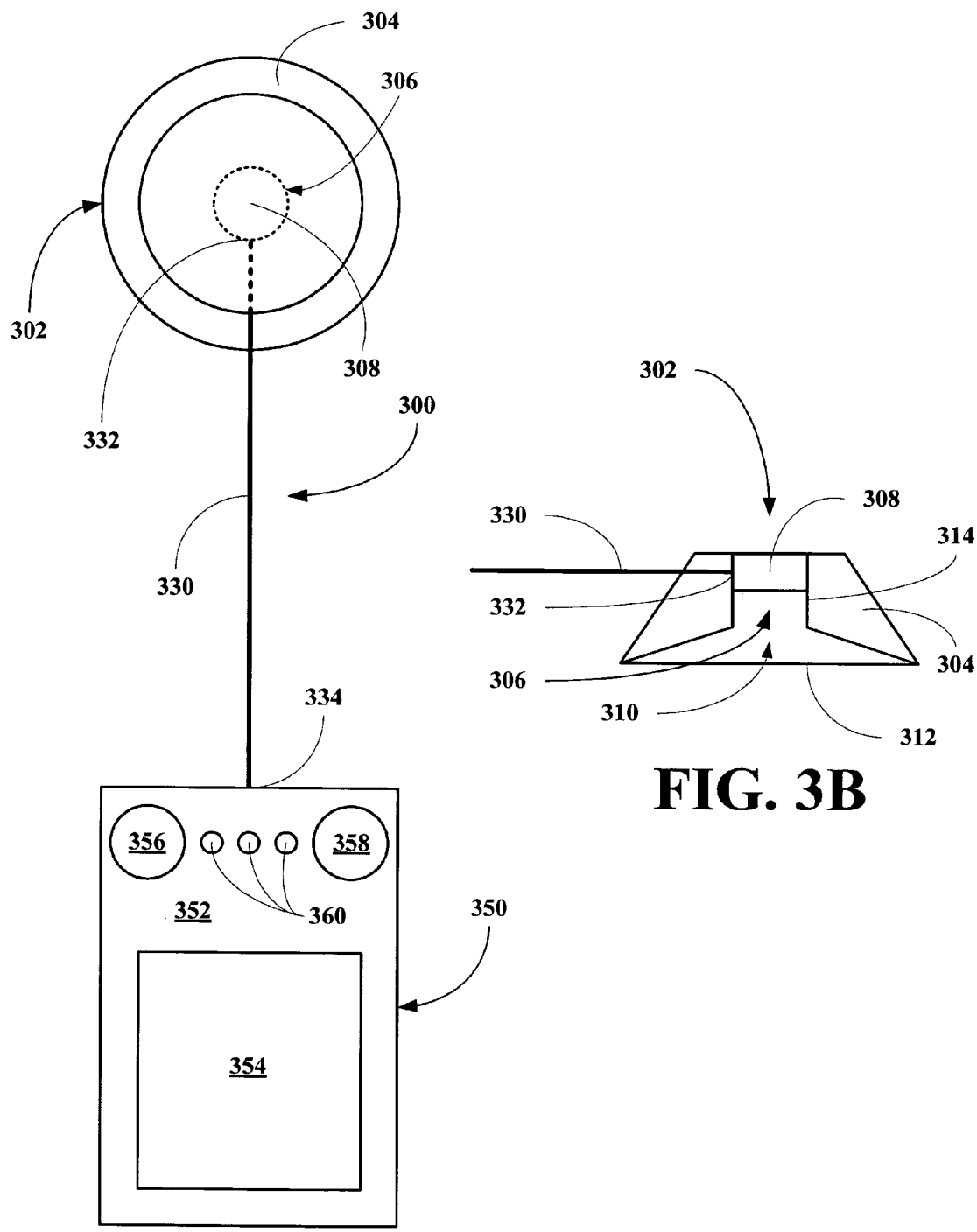
FIGS. 3A&B depict another embodiment of an apparatus to confirm proper placement of an endotracheal tube in a patient.

Referring now to FIGS. 3A&B, an embodiment of an apparatus of this invention, generally 300, is shown to include an audio receiving unit 302 having a body 304. The receiving unit 302 also includes an acoustic cavity 310 having an acoustic channel 314. In a center 306 of the channel 316 is mounted a receiver 308. The receiving unit 302 may also include a diaphragm 312 so that the cavity 310 is defined between the diaphragm 312 and the receiver 308.

The apparatus 300 also includes a signal cable 330 connected at a first end 332 to the microphone 308 and at a second end 334 to an audio processing unit 350.

The processing unit 350 include a housing 352. The processing unit 352 can include one or more of a visual display component 354, a speaker 356, a tactile component 358 or indicator lights 360. The visual display component 354 is adapted to produce a visual image corresponding to the received audio signal and an analysis of whether the received audio signal evidences a proper tube placement. The visual display can be a display of the received signal relative to a signal from a properly placed tube or a display of the received signal and a message indicated proper or improper placement. The speaker 356 is adapted to produce an audio signal either corresponding to the received audio signal or to produce an indication that the signal corresponds either to a proper or improper placement of the tube such as a voice saying good or bad placement. The tactile component 358 is adapted to produce touch cognizable pulses to indicate proper or improper tube placement. The indicator lights 360 are adapted to produce lights indicating proper or improper tube placement. The processing unit 350 can include all of any combination of these output components. Moreover, each output component can be designed not only to evidence proper tube placement, but to also evidence the nature of the improper tube placement such as placement in the esophagus, a placement ventilating a single lung, a placement with an improper seal, etc.

Figures 4A, 4B:
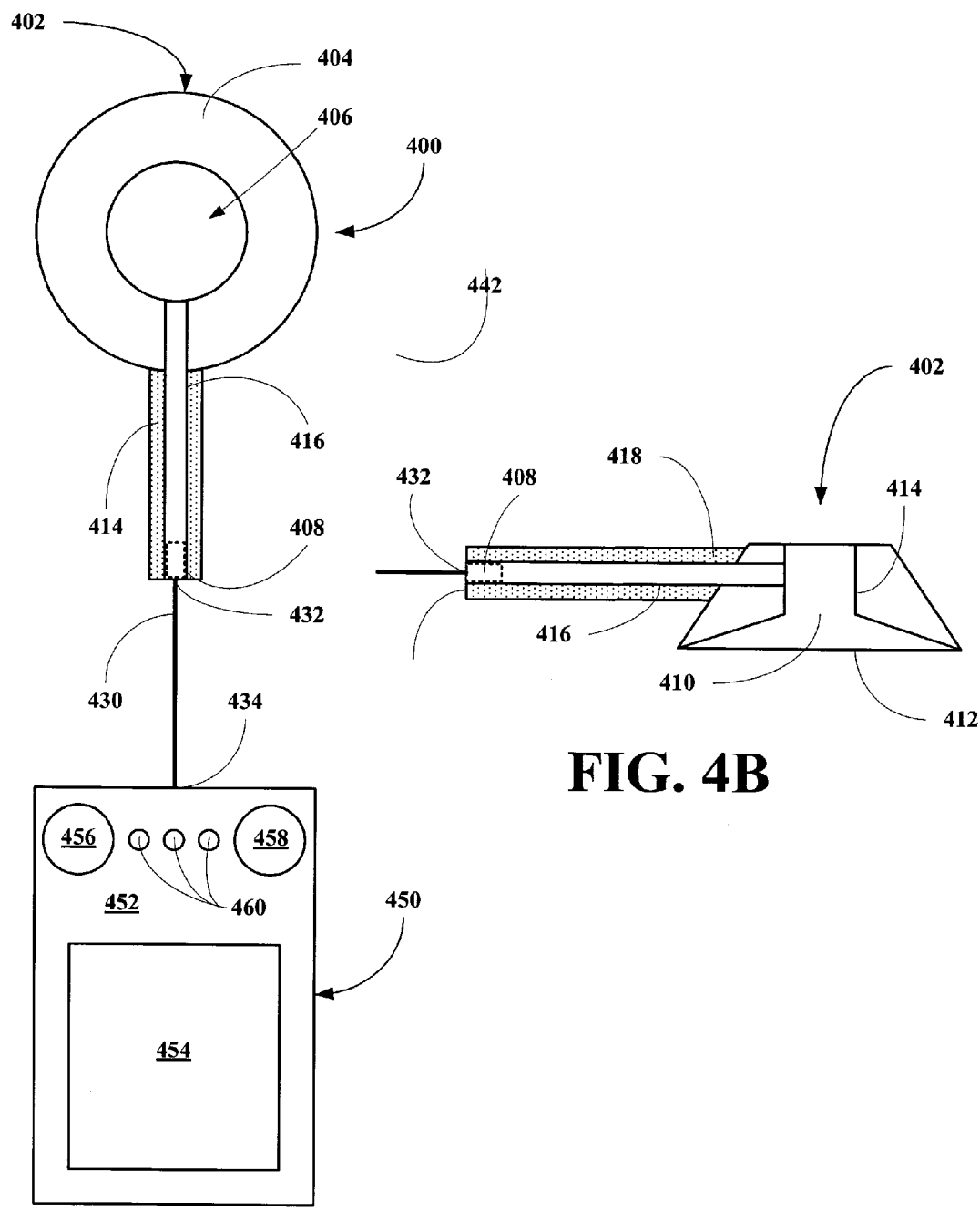
FIGS. 4A&B depict another embodiment of an apparatus to confirm proper placement of an endotracheal tube in a patient.

Referring now to FIGS. 4A&B, an embodiment of an apparatus of this invention, generally 400, is shown to include an audio receiving unit 402 having a body 404. The receiving unit 402 also includes an acoustic cavity 410 having an acoustic channel 414. The receiving unit 402 may also include a diaphragm 412 so that the cavity 410 is defined between the diaphragm 412 and the channel 414. The apparatus 400 also includes a tube 416 extending out from the channel 414. In a distal end 406 of the tube 416 is mounted a receiver 408. The tube 414 may optionally be surrounded by a low-density foam 418 to reduce acoustic artifacts from the patient and/or the operating room.

The apparatus 400 also includes a signal cable 430 connected at a first end 432 to the receiver 408 and at a second end 434 to an audio processing unit 450.

The processing unit 450 include a housing 452. The processing unit 452 can include one or more of a visual display component 454, a speaker 456, a tactile component 458 or indicator lights 460. The visual display component 454 is adapted to produce a visual image corresponding to the received audio signal and an analysis of whether the received audio signal evidences a proper tube placement. The visual display can be a display of the received signal relative to a signal from a properly placed tube or a display of the received signal and a message indicated proper or improper placement. The speaker 456 is adapted to produce an audio signal either corresponding to the received audio signal or to produce an indication that the signal corresponds either to a proper or improper placement of the tube such as a voice saying good or bad placement. The tactile component 458 is adapted to produce touch cognizable pulses to indicate proper or improper tube placement. The indicator lights 460 are adapted to produce lights indicating proper or improper tube placement. The processing unit 450 can include all of any combination of these output components. Moreover, each output component can be designed not only to evidence proper tube placement, but to also evidence the nature of the improper tube placement such as placement in the esophagus, a placement ventilating a single lung, a placement with an improper seal, etc.

Compact Embodiments

Figure 5:
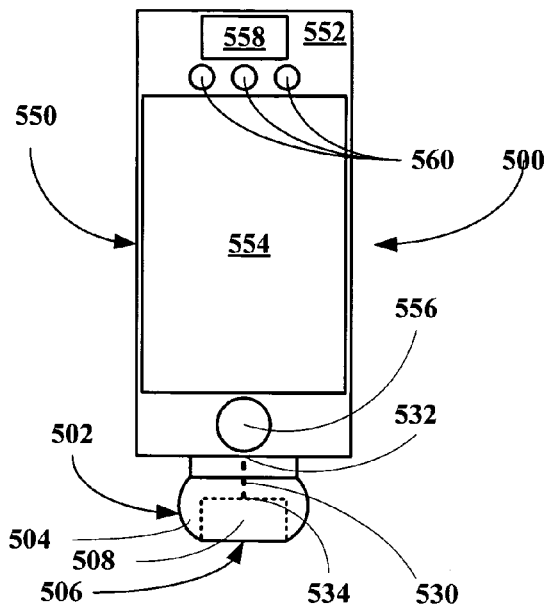
FIG. 5 depicts a compact embodiment of an apparatus to confirm proper placement of an endotracheal tube in a patient.

Referring now to FIG. 5, a compact embodiment of an apparatus of this invention, generally 500, is shown to include an audio receiving unit 502 having a oval shaped body 504. In a center 506 of the body 504 is mounted an audio receiver 508. In this embodiment 500, the receiver 508 is designed to come into contact with the skin of the patient. A fluid such as the fluid used in ultrasound can be used to improve audio contact between the receiver and the skin.

The apparatus 500 also includes a signal cable 530 connected at a first end 532 to the receiver 508 and at a second end 534 to an audio processing unit 550.

The processing unit 550 include a housing 552. The processing unit 552 can include one or more of a visual display component 554, a speaker 556, a tactile component 558 or indicator lights 560. The visual display component 554 is adapted to produce a visual image corresponding to the received audio signal and an analysis of whether the received audio signal evidences a proper tube placement. The visual display can be a display of the received signal relative to a signal from a properly placed tube or a display of the received signal and a message indicated proper or improper placement. The speaker 556 is adapted to produce an audio signal either corresponding to the received audio signal or to produce an indication that the signal corresponds either to a proper or improper placement of the tube such as a voice saying good or bad placement. The tactile component 558 is adapted to produce touch cognizable pulses to indicate proper or improper tube placement. The indicator lights 560 are adapted to produce lights indicating proper or improper tube placement. The processing unit 550 can include all of any combination of these output components. Moreover, each output component can be designed not only to evidence proper tube placement, but to also evidence the nature of the improper tube placement such as placement in the esophagus, a placement ventilating a single lung, a placement with an improper seal, etc.

Figure 6:
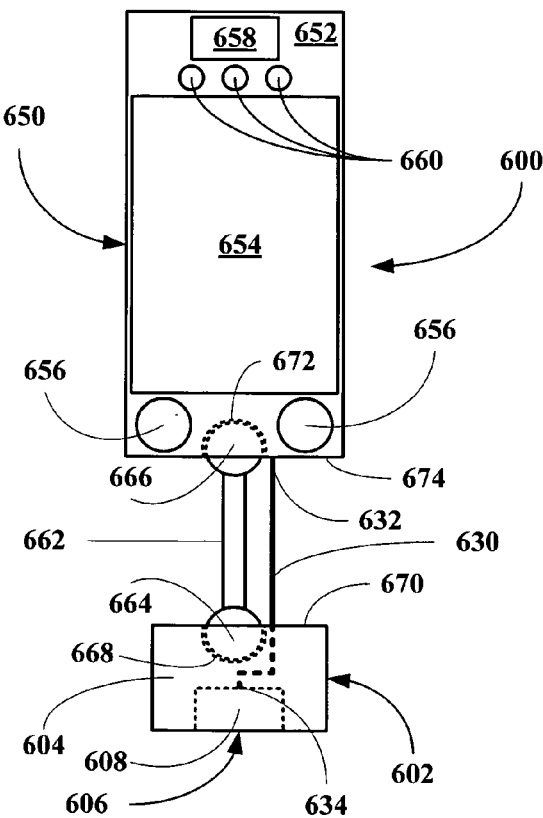
FIG. 6 depicts another compact embodiment of an apparatus to confirm proper placement of an endotracheal tube in a patient.

Referring now to FIG. 6, another compact embodiment of an apparatus of this invention, generally 600, is shown to include an audio receiving unit 602 having a oval shaped body 604. In a center 606 of the body 604 is mounted an audio receiver 608. In this embodiment 600, the receiver 608 is designed to come into contact with the skin of the patient. A fluid such as the fluid used in ultrasound can be used to improve audio contact between the receiver and the skin.

The apparatus 600 also includes a signal cable 630 connected at a first end 632 to the receiver 608 and at a second end 634 to an audio processing unit 650.

The processing unit 650 include a housing 652. The processing unit 652 can include one or more of a visual display component 654, a speaker 656, a tactile component 658 or indicator lights 660. The visual display component 654 is adapted to produce a visual image corresponding to the received audio signal and an analysis of whether the received audio signal evidences a proper tube placement. The visual display can be a display of the received signal relative to a signal from a properly placed tube or a display of the received signal and a message indicated proper or improper placement. The speaker 656 is adapted to produce an audio signal either corresponding to the received audio signal or to produce an indication that the signal corresponds either to a proper or improper placement of the tube such as a voice saying good or bad placement. The tactile component 658 is adapted to produce touch cognizable pulses to indicate proper or improper tube placement. The indicator lights 660 are adapted to produce lights indicating proper or improper tube placement. The processing unit 650 can include all of any combination of these output components. Moreover, each output component can be designed not only to evidence proper tube placement, but to also evidence the nature of the improper tube placement such as placement in the esophagus, a placement ventilating a single lung, a placement with an improper seal, etc.

The processing unit 650 is connected to the receiving unit 602 via a connecting rod or shaft 662 having two ball 664 and 666 disposed on each end. One ball 664 is adapted to be received into a socket 668 disposed in a proximal end 670 of the receiving body 602. The second ball 666 is adapted to be received into a second socket 672 disposed in a proximal end 674 of the processing body 652. In the embodiment 600, the shaft 662, the two balls 664 and 666 and the two sockets 668 and 672 are designed to allow the processing unit 650 to be swivelled relative to the receiving unit 602 to a convenient position for viewing, hearing or touching.

Figure 7:
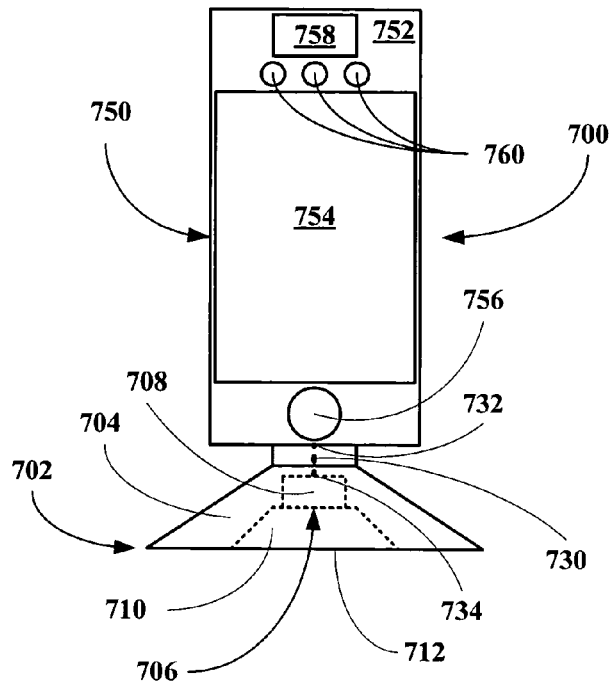
FIG. 7 depicts another compact embodiment of an apparatus to confirm proper placement of an endotracheal tube in a patient.

Referring now to FIG. 7, a compact embodiment of an apparatus of this invention, generally 700, is shown to include an audio receiving unit 702 having a oval shaped body 704. In a center 706 of the body 704 is mounted an audio receiver 708. The receiving unit 702 also includes an audio cavity 710. The receiving unit 702 may also include a diaphragm 712 so that the cavity 710 is defined between the diaphragm 712 and the receiver 708.

The apparatus 700 also includes a signal cable 730 connected at a first end 732 to the receiver 708 and at a second end 734 to an audio processing unit 750.

The processing unit 750 include a housing 752. The processing unit 752 can include one or more of a visual display component 754, a speaker 756, a tactile component 758 or indicator lights 760. The visual display component 754 is adapted to produce a visual image corresponding to the received audio signal and an analysis of whether the received audio signal evidences a proper tube placement. The visual display can be a display of the received signal relative to a signal from a properly placed tube or a display of the received signal and a message indicated proper or improper placement. The speaker 756 is adapted to produce an audio signal either corresponding to the received audio signal or to produce an indication that the signal corresponds either to a proper or improper placement of the tube such as a voice saying good or bad placement. The tactile component 758 is adapted to produce touch cognizable pulses to indicate proper or improper tube placement. The indicator lights 760 are adapted to produce lights indicating proper or improper tube placement. The processing unit 750 can include all of any combination of these output components. Moreover, each output component can be designed not only to evidence proper tube placement, but to also evidence the nature of the improper tube placement such as placement in the esophagus, a placement ventilating a single lung, a placement with an improper seal, etc.

Figure 8:
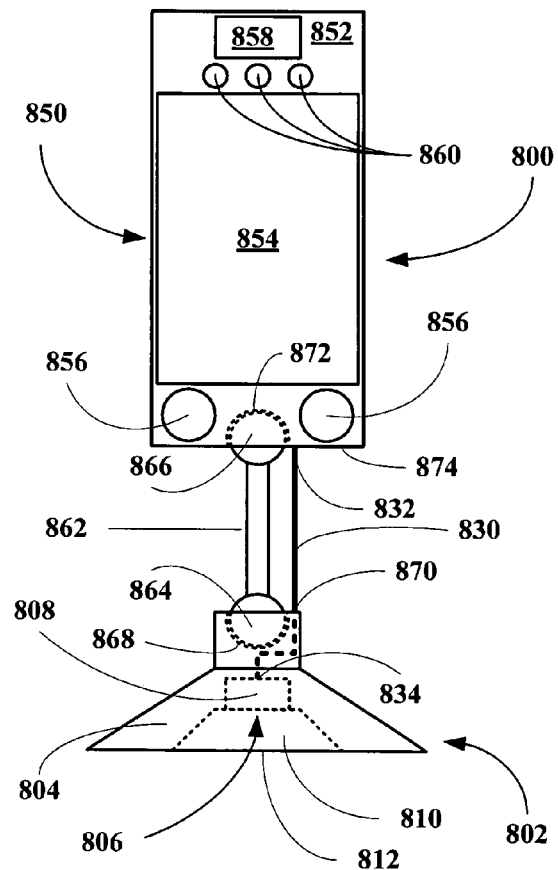
FIG. 8 depicts another compact embodiment of an apparatus to confirm proper placement of an endotracheal tube in a patient.

Referring now to FIG. 8, another compact embodiment of an apparatus of this invention, generally 800, is shown to include an audio receiving unit 802 having a oval shaped body 804. In a center 806 of the body 804 is mounted an audio receiver 808. The receiving unit 802 also includes an audio cavity 810. The receiving unit 802 may also include a diaphragm 812 so that the cavity 810 is defined between the diaphragm 812 and the receiver 808.

The apparatus 800 also includes a signal cable 830 connected at a first end 832 to the receiver 808 and at a second end 834 to an audio processing unit 850.

The processing unit 850 include a housing 852. The processing unit 852 can include one or more of a visual display component 854, a speaker 856, a tactile component 858 or indicator lights 860. The visual display component 854 is adapted to produce a visual image corresponding to the received audio signal and an analysis of whether the received audio signal evidences a proper tube placement. The visual display can be a display of the received signal relative to a signal from a properly placed tube or a display of the received signal and a message indicated proper or improper placement. The speaker 856 is adapted to produce an audio signal either corresponding to the received audio signal or to produce an indication that the signal corresponds either to a proper or improper placement of the tube such as a voice saying good or bad placement. The tactile component 858 is adapted to produce touch cognizable pulses to indicate proper or improper tube placement. The indicator lights 860 are adapted to produce lights indicating proper or improper tube placement. The processing unit 850 can include all of any combination of these output components. Moreover, each output component can be designed not only to evidence proper tube placement, but to also evidence the nature of the improper tube placement such as placement in the esophagus, a placement ventilating a single lung, a placement with an improper seal, etc.

The processing unit 850 is connected to the receiving unit 802 via a connecting rod or shaft 862 having two ball 864 and 866 disposed on each end. One ball 864 is adapted to be received into a socket 868 disposed in a proximal end 870 of the receiving body 802. The second ball 866 is adapted to be received into a second socket 872 disposed in a proximal end 874 of the processing body 852. In the embodiment 800, the shaft 862, the two balls 864 and 866 and the two sockets 868 and 872 are designed to allow the processing unit 850 to be swivelled relative to the receiving unit 802 to a convenient position for viewing, hearing or touching.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

The invention claimed is:

1. A method for confirming proper placement endotracheal tube comprising the steps of:
    providing an apparatus comprising:
        an audio receiving unit including a receiver adapted to be placed on a site of a patient's body and to receive sounds generated from a pilot tube of an endotracheal tube,
        an audio processing unit adapted to receive an audio signal detected by the audio receiver and to verify a proper placement of the endotracheal tube in the patient based on characteristics of the audio signal; and
        a signal cable interconnecting the receiver and the processing unit;
    placing the audio receiving unit on a site of a patient's skin;
    inserting an endotracheal tube into the patient;
    inflating a pilot balloon of the endotracheal tube, which is filled with a gas and liquid mixture;
    squeezing the balloon generating a crepitus sound,
    detecting the sound in the receiver,
    producing a signal from the receiver,
    determining, in the processing unit, if the signal evidences proper or improper endotreachal tube placement,
    generating a cognizable human output corresponding to the placement, and
    if the placement is improper, repositioning the tube until the signal evidences proper placement.

2. The method of claim 1, wherein the site is a suprasternal notch.

3. The method of claim 1, wherein the receiving unit further includes an audio cavity.

4. The method of claim 3, wherein the receiving unit further includes a diaphragm so that the cavity is defined between the diaphragm and the receiver.

5. The method of claim 3, wherein the audio cavity includes a channel and the receiver is mounted in a center of the channel.

6. The method of claim 5, wherein the audio cavity includes a channel and the receiver is mounted in a center of the channel.

7. The method of claim 1, wherein the processing unit includes at least one human cognizable output component, where the at least one human cognizable output component generates a human cognizable output evidencing proper or improper endotracheal tube placement.

8. The method of claim 7, wherein the output further evidences a nature of an improper endotracheal tube placement.

9. The method of claim 1, wherein the human cognizable output components are selected from the group consisting of a speaker, a display, indicator lights, a tactile device, vibrator, and mixtures or combinations thereof.

* * * * *